United States Patent [19]
Collins et al.

[11] Patent Number: 5,184,614
[45] Date of Patent: Feb. 9, 1993

[54] IMPLANTABLE HAEMODYNAMICALLY RESPONSIVE CARDIOVERTING/DEFIBRILLATING PACEMAKER

[75] Inventors: Kenneth A. Collins, Neutral Bay; Philip J. Maker, North Ryde; Matthew S. Walker, Cronulla, all of Australia

[73] Assignee: Telectronics Pacing Systems, Inc., Englewood, Colo.

[21] Appl. No.: 600,419

[22] Filed: Oct. 19, 1990

[51] Int. Cl.$^5$ .............................. A61N 1/365
[52] U.S. Cl. ...................... 128/419 PG; 128/419 D
[58] Field of Search ............ 128/419 PG, 419 D, 670, 128/734, 419 PT

[56] References Cited

U.S. PATENT DOCUMENTS

| | | | |
|---|---|---|---|
| 3,614,955 | 10/1971 | Mirowski et al. | 128/419 D |
| 3,942,536 | 3/1976 | Mirowski et al. | 128/419 D |
| 4,096,866 | 6/1978 | Fischell | 128/419 PG |
| 4,140,131 | 2/1979 | Dutcher et al. | 128/419 PT |
| 4,248,238 | 2/1981 | Joseph | 128/419 PG |
| 4,291,699 | 9/1981 | Geddes et al. | 128/419 D |
| 4,416,282 | 11/1983 | Saulson et al. | 128/419 PG |
| 4,527,568 | 7/1985 | Rickards | 128/419 PG |
| 4,774,950 | 10/1988 | Cohen | 128/419 D |
| 4,830,006 | 5/1989 | Haluska et al. | 128/419 PG |
| 4,869,252 | 9/1989 | Gilli | 128/419 PG |
| 4,880,004 | 11/1989 | Baker et al. | 128/419 PG |
| 4,895,151 | 1/1990 | Grevis et al. | 128/419 PG |
| 4,932,406 | 6/1990 | Berkovits | 128/419 PG |
| 4,944,298 | 7/1990 | Sholder | 128/419 PG |
| 4,977,896 | 12/1990 | Robinson et al. | 128/731 |
| 5,003,975 | 4/1991 | Hafelfinger et al. | 128/419 PG |
| 5,083,563 | 1/1992 | Collins | 128/419 D |
| 5,097,831 | 3/1992 | Lekholm | 128/419 PG |
| 5,105,810 | 4/1992 | Collins et al. | 128/419 D |

FOREIGN PATENT DOCUMENTS

| | | |
|---|---|---|
| 0182197 | 5/1986 | European Pat. Off. . |
| 0253505 | 1/1988 | European Pat. Off. . |
| 0335977 | 10/1989 | European Pat. Off. . |
| 350160 | 1/1990 | European Pat. Off. ..... 128/419 PG |
| 2198044 | 6/1988 | United Kingdom . |

OTHER PUBLICATIONS

W. Verrydt et al., "Automatic Defibrillator, Antitachy Pacemaker and Cardioverter", *Computers in Cardiology*—IEEE, Oct. 7-10, 1986, Boston, Mass., U.S.A., pp. 45-48.

H. Makino et al., "Implantable Defibrillator With High-Output Pacing Function After Defibrillation", *Proceedings of the IEEE*, vol. 76, No. 9, Sep. 1988, New York, U.S., pp. 1187-1192.

*Primary Examiner*—Kyle L. Howell
*Assistant Examiner*—Kennedy J. Schaetzle
*Attorney, Agent, or Firm*—Gottlieb, Rackman & Reisman

[57] ABSTRACT

An implantable device for the treatment of malfunctions of a patient's heart is disclosed. The device includes a first modality for sensing an electrical function in the patient's heart and providing a first signal representative of such electrical function, and a second modality for sensing an haemodynamic function in the patient's heart and providing a second signal representative of such haemodynamic function. The device is also provided with first circuitry that is primarily responsive to the signal from one of the sensing modalities for analyzing the state of the heart's function and providing any required electrical shock therapy to the heart. The device further includes second circuitry that is responsive to uncertainty in regard to the therapy to be provided by the first circuitry and is operative to change the responsiveness of the first circuitry to the signal provided by the other of the sensing modalities for controlling the therapy that is to be provided to the heart. A corresponding method of treating malfunctions of a patient's heart is also disclosed.

31 Claims, 9 Drawing Sheets

| RATE | RVPPF | RVFPPA | THERAPY |
|---|---|---|---|
| <=120 | >60% | >80% | Normal Pacing Therapy |
| <=120 | <60% | <80% | Pacing Optimising Algorithm |
| >120 | >50% | >50% | Antitachycardia Pacing |
| >120 | >30% +<=50% | >30% +<=50% | Cardioversion |
| >120 | <=30% | <=30% | Defibrillation |

Fig. 5. Paced Rhythm: 240 b.p.m.

IMPLANTABLE HAEMODYNAMICALLY RESPONSIVE CARDIOVERTING/DEFIBRILLATING PACEMAKER

BACKGROUND OF INVENTION

This invention relates to an implantable cardioverting/defibrillating pacemaker and, more particularly, to a pacemaker of this type that is responsive both to an electrically derived heart rate and to an haemodynamic parameter.

An implantable haemodynamic cardioverting/defibrillating pacemaker is disclosed in U.S. patent application, No. 481,364 to K. A. Collins, filed Feb. 16, 1990, and entitled "An Implantable Automatic and Haemodynamically Responsive Cardioverting/Defibrillating Pacemaker," now U.S. Pat. No. 5,083,563 which is assigned to the assignee of the present invention, and is incorporated herein by reference. The pacemaker of said application No. 481,364 overcomes many of the problems of false or inappropriate delivery of therapy that arise out of a reliance solely upon the sensing of the electrical activity of the heart as a means of determining the state of cardiac function.

Among the significant problems that face such an implantable device are to control the quality of its input signals, and to determine when there has been a failure of the input transducing system. These involve three components: first, deciding when a sensing system has failed to properly function; second, properly controlling the gain of the input amplifiers; and third, resolving conflicting information when more than one method of transduction is being used.

The failure of a lead which interconnects the sensing element and the pacemaker, due to breakage of the conductor, is possible. More commonly, failures in sensing are a result of inappropriate input amplifier gain. It is well known that the signal amplitude of the electrocardiogram (ECG) signal varies, especially during ventricular fibrillation (VF), and that an inability to sense the ECG can result in a failure of the defibrillator to revert VF, despite mechanisms for altering the gain of the amplifiers to suit the signal. This is taught by Williams et al. in their article "Automatic Implantable Cardioverter-Defibrillator-Related Complications", JACC, Vol. 15, Page 55A (1990).

A related sensing error can occur due to transient increases in the noise injected into the ECG sensing system. Such bursts of noise can be induced by electromagnetic sources such as electric motors They can be responsible for temporary periods of uncertainty in the diagnosis of the state of the hearts function when it is assessed by electrically derived rate criteria.

For cardioverting/defibrillating pacemakers that use more than one sensing modality, there is a need both to have systems to detect the various forms of sensing system failure and to have methods for initiating appropriate therapy in the face of such failure.

Mirowski et al., in U.S. Pat. Nos. 3,614,955 and 3,942,536, describe systems that sense heart function using the peak of the right ventricular pressure waveform. Devices of this kind, have no means of determining whether or not their sensing circuits are functioning.

A device disclosed in U.S. Pat. No. 4,774,950 to Cohen is an haemodynamic cardioverting/defibrillator. This device also lacks any mechanism by which to monitor its own function. It also lacks any means or method for deciding upon device function in the event that there is either a failure of or a temporary uncertainty in the diagnosis of the state of the heart in one of its sensing modalities.

As indicated earlier, two problems associated with implantable cardioverting/defibrillating pacemaker devices are to control the quality of its input signals and to determine when there has been a failure of the input transducing system. These involve three components, firstly, deciding when a sensing system has failed to properly function; secondly, properly controlling the gain of the input amplifier; and thirdly, being able to resolve conflicting information when more than one method of transduction is being used.

The first component is the easiest to resolve. It is common practice to measure the impedance of pacing electrodes to determine if they are properly sited. Dutcher et al., in U.S. Pat. No. 4,140,131, discloses one method of implementing such an impedance check in an implantable pacemaker. This method does not progress far enough for a device that has more than one means of sensing heart function. The Dutcher et al. method can only determine whether or not the impedance of the pacing electrode is within operational limits. It cannot determine whether or not pacing is still possible; nor can it switch to an alternate sensing mode in the event of failure of the primary sensing modality; nor can it be used to adjust the amplifier gain of the input amplifier.

In European Patent Application No. 89305623, dated Jun. 5, 1989, Baker et al. reveal a method and means of implementing automatic gain control that is based on the amplitude of the ECG signal that is being presented. This system suffers from a basic problem that is common to all systems that use the sensed signal as the means for establishing the gain on the sensing amplifiers, namely that the detected signal can be so small as to be lost in noise. Any amplifier gain applied to the desired signal is also applied to the noise present in the sensing system. Increasing the gain of the sensing amplifiers in such situations, despite anti-noise filtering, will lead to the inappropriate sensing of noise spikes as if they were QRS complexes in the ECG signal.

It is, therefore, a primary object of the present invention to provide a cardioverting/defibrillating pacemaker device which includes a second sensing modality and which is capable of determining the appropriate action to take in the event of a failure of or uncertainty in the diagnosis of cardiac state in one of its two or more sensing systems.

An additional object of the invention is to provide a two sensing modality cardioverting/defibrillating pacemaker device which utilizes electrically derived timing events to diagnose heart function in the event of pressure signal failure and which, in the event of failure of the ECG sensing system, uses a ventricular pressure (VP) signal to determine the state of function of the heart.

Another object of the invention is to provide a cardioverting/defibrillating pacemaker device which can determine whether a malfunction is in the sensing circuit and/or in the pacing circuitry by reference to the evoked response seen in the ventricular pressure (VP) waveform, and to use this information to alter its own therapy logic to best be able to deal with the detected malfunction.

A further object of the invention is to provide a cardioverting/defibrillating pacemaker device to implement a form of gain control that does not rely upon the signal being sensed to determine the state of heart function, while it ensures that the gain of the sensing amplifiers is optimal.

A still further object of the invention is to provide, in a cardioverting/defibrillating pacemaker device that utilizes two sensing modalities, the ability for the pacemaker to use one sensing modality to monitor the function of the heart while the gain of the other modality is being altered. Amplifier gain can thus be controlled and one of the two systems deactivated when an adequate signal cannot be obtained despite maximal amplifier gain.

Yet another object of the invention is to provide a cardioverting/defibrillating pacemaker device having two sensing modalities therein that will provide a tactile warning in the event of one of the two sensing modalities being deactivated, and will inform the supporting physician of such deactivation via telemetry on the next occasion upon which he interrogates the device.

Further objects and advantages of this invention will become apparent as the following description proceeds.

SUMMARY OF TERMS

| | |
|---|---|
| ATP | Antitachycardia Pacing. |
| ECG | The ECG is, strictly speaking, a graphical representation of the electrical activity of the heart. However, the term ECG is used loosely to refer to the electrical activity of heart. The electrical activity of the heart can be sensed either on the surface of the skin, or on or in the heart. |
| L (Left) | Used to signify that an acronym refers to the left side of the heart as in: LVFPPA - Left Ventricular Filtered Peak-to-Peak Amplitude (VFPPA); LVP - Left Ventricular Pressure (VP); LVPPF - Left Ventricular Peak Pressure Function (VPPF); etc. |
| R (Right) | Used to signify that an acronym refers to the right side of the heart as in: RVFPPA Right Ventricular Filtered Peak-to-Peak Amplitude (VFPPA); RVP - Right Ventricular Pressure (VP); RVPPF - Right Ventricular Peak Pressure Function (VPPF); etc. |
| VF | Ventricular Fibrillation. |
| VFPPA | Ventricular Filtered Peak-to-Peak Pressure Amplitude. |
| VP | Ventricular Pressure. |
| VPPF | Ventricular Peak Pressure Function. |
| VT | Ventricular Tachycardia. |

TERMINOLOGY

A pacemaker is any device capable of electrically stimulating the heart to contract. Most such devices can also sense the electrical activity of a contracting heart and react to alterations in its electrical function. Most such devices are implanted and, if programmable, are interacted with via a telemetric link.

Rate Responsive or physiological pacemakers are pacemaking devices that are able to sense and respond to some indicator of increased tissue oxygen demand, for example respiratory rate. They respond by altering the paced heart rate to meet the changes in oxygen requirements.

A cardioverter/defibrillator is any device that can sense the presence of tachyarrhythmias and deliver an electric shock to a heart in order to revert it back to a normal rhythm. The difference between a cardioverter and a defibrillator lies only in the amount of energy delivered to the heart. Cardioversion is usually used to refer to low energy shocks, and defibrillation to high energy shocks A cardioverter/defibrillator is usually capable of supplying energies in a range of less than one joule to more than forty joules These shocks may or may not be synchronized with the R-wave of the ECG A cardioverting/defibrillating pacemaker is a device that can perform cardioverting, defibrillating and pacemaking functions. When referred to herein, it applies equally to devices that deliver their energy synchronously with a detected R-wave and to devices that do not. When used, the term will usually apply to devices that electrically sense and/or stimulate via electrodes in the right ventricle and atrium. However, it can also apply to devices that do so only in the right ventricle, in the right atrium alone, in multiple heart chambers via epicardial patches or leads, or via other sense/stimulation configurations.

Antitachycardia pacing (ATP) is a technique implemented in some pacemaking devices Its aim is to pace a rapidly and abnormally beating heart back into a more normal rhythm. Its use implies that the tachyarrhythmia detected is considered not to be so sufficiently haemodynamically compromising that it will endanger vital organs within the anticipated treatment time. ATP may produce a more malignant tachyarrhythmia; for example, ventricular tachycardia (VT) may be paced into ventricular fibrillation (VF). For this reason ATP is normally implemented only when there is the option to use cardioversion/defibrillation therapy.

Wherever reference is made herein to a device that senses the right ventricular ECG (RVECG), and/or the right atrial ECG (RAECG), and the right ventricular pressure (RVP), the latter to derive the right ventricular FPPA (RVFPPA) and VPPF (RVPPF), and that uses this information to implement bradycardia pacing, antitachycardia pacing or defibrillation, it should be understood that the device can also sense and respond to the left ventricular ECG, and/or left atrial ECG, and left VP in a similar fashion, i.e., via deriving LVFPPA and LVPPF.

Capture is used to refer to the entrainment of the heart rhythm with pacing pulses. In this respect the evoked responses are the responses of the heart, once captured, to the pacing pulses delivered. There are many possible evoked responses: the main meaning being the electrophysiological response. In this disclosure the evoked response referred to is usually the initiation of ventricular contraction, as witnessed by the development of a pressure pulse within the ventricle.

SUMMARY OF THE INVENTION

Briefly stated, and in accordance with one embodiment of the invention, there is provided an implantable device for treating malfunctions of a patient's heart. The device includes a first modality for sensing an electrical function in the patient's heart and providing a first signal representative of such electrical function, and a second modality for sensing an haemodynamic function in the patient's heart and providing a second signal representative of such haemodynamic function. The device is also provided with a first means that is primarily responsive to the signal from one of the sensing modalities for analyzing the state of the heart's function and providing any required electrical shock therapy to the heart. The device further includes a second means that is responsive to uncertainty in regard to the therapy to be provided by the first means and is operative to change the responsiveness of the first means to the signal provided by the other of the sensing modalities for controlling the therapy that is to be provided to the heart.

In accordance with another embodiment, the invention incorporates a method of treating malfunctions of a patient's heart The method comprises the steps of implanting in a patient a device having a first modality for sensing an electrical function in the patient's heart and providing a first signal representative of such electrical function, and a second modality for sensing an haemodynamic function in the patient's heart and providing a second signal representative of such haemodynamic function; analyzing one of such signals to determine the state of the heart's function and decide on any required electrical shock therapy to be provided to the heart; and, in the event of uncertainty in regard to the therapy to be provided as a result of such analysis, analyzing the other of such signals to decide on the electrical shock therapy to be provided to the heart.

BRIEF DESCRIPTION OF THE DRAWINGS

While the specification concludes with claims particularly pointing out and distinctly claiming the subject matter of this invention, it is believed that the invention will be better understood from the following description, taken in conjunction with the accompanying drawings, in which:

DESCRIPTION OF THE PREFERRED EMBODIMENTS

Figures 1, 2:
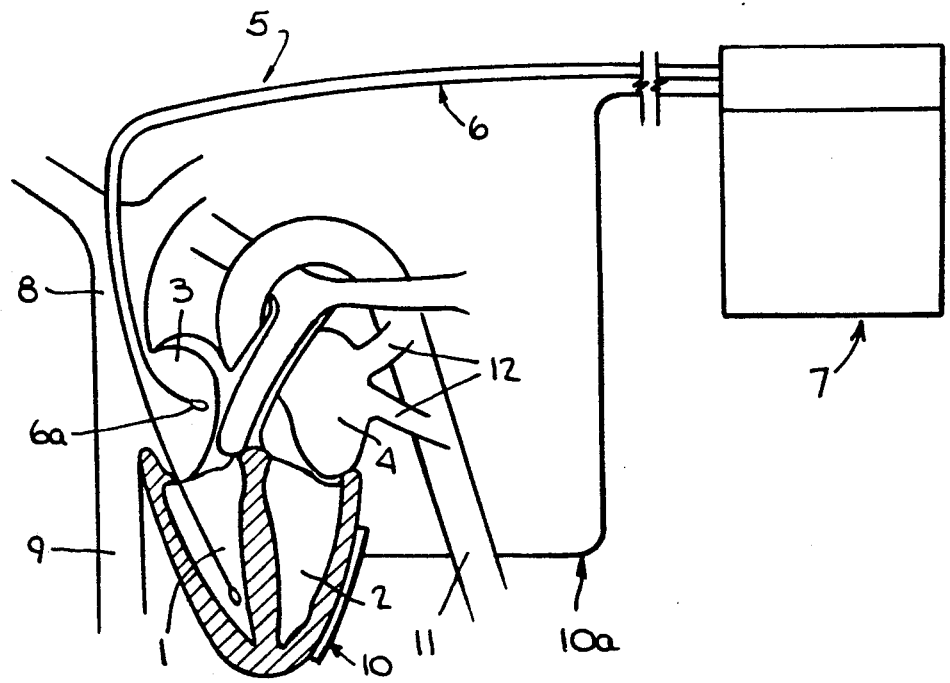
FIG. 1 is a table of representative RVFPPA and RVPPF values.
FIG. 2 is a schematic diagram of an implanted cardioverting/defibrillating pacemaker device in accordance with the present invention, positioned in the patient's body and showing electrical leads which interconnect the heart and the device.

Referring to FIG. 1, the type of therapy that is typically selected, in accordance with the invention, is set forth as a function of heart rate, RVPPF and RVFPPA. Heart rate is expressed in beats per minute. RVPPF and RVFPPA are expressed as a percentage of resting value. It should be noted that the values given in FIG. 1 are typical percentage values only, and that the values for a given recipient will be determined by electrophysiological studies conducted at the time of implantation.

Referring to FIG. 2, the invention is described herein in connection with its use in an implantable cardioverting/defibrillating pacemaker device, shown generally at 7, which is responsive both to an electrically derived heart rate and to a haemodynamic parameter, for example the device disclosed in the aforesaid Collins patent application No. 481,364. The device 7, which is preferably implemented as a dual chamber device but may also be implemented as a single chamber device, is permanently implanted in accordance with known practices at a point remote from the cardiac cavity, and is connected to the heart 13 by various leads. Thus, referring to FIGS. 2 and 3, a dual lead 5, which includes an ECG signal sensor lead 14 and a pressure sensor lead 15, interconnects an ECG signal sensor 14a and a pressure sensor 15a located in the right ventricle 1 of the patient's heart with the device 7. Similarly, one or more epicardial defibrillation patch(es), shown generally at 10, are connected to the device 7 by corresponding lead(s) 10a, and an atrial ECG signal sensor 6a positioned in the right atrium 3 is connected to the device 7 by an ECG lead 6. Other parts of the heart and its associated heart vessels include the left ventricle 2, the left atrium 4, the superior vena cava 8, the inferior vena cava 9, the aorta 11 and the pulmonary vessels 12.

Figure 3:
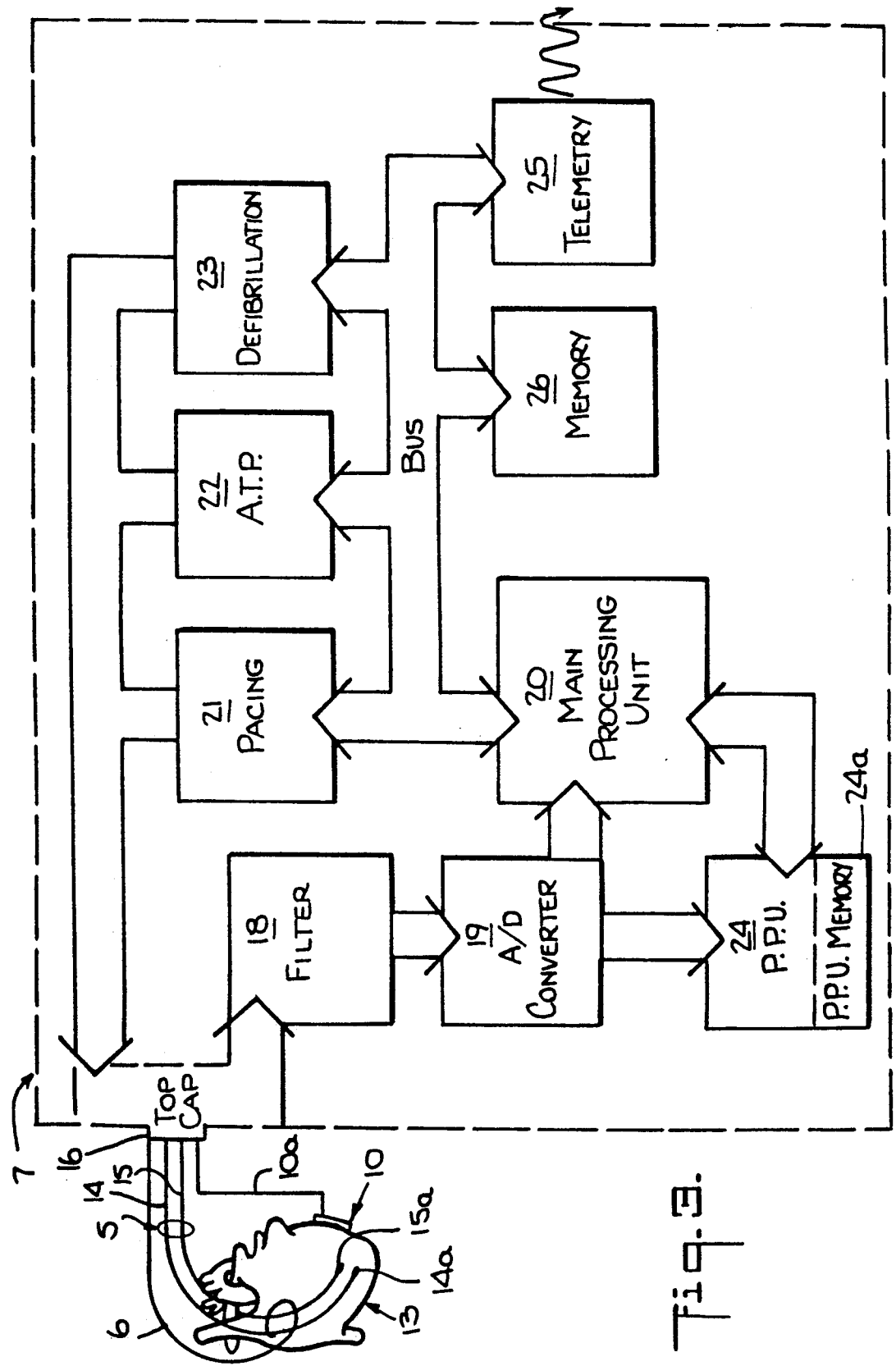
FIG. 3 is a block diagram of the device shown in FIG. 2, with blocks thereof representing either discrete components or logic units within one or more microprocessors of the device.

Referring more particularly to FIG. 3 the major circuits and logical units of the device have there been illustrated. In the preferred embodiment of this invention, the analog signals sensed by the various sensors in the heart are delivered by the leads 6, 10a, 14 and 15 through the top cap 16 of the device 7 to a high pass filter 18, wherein the VP waveform is filtered to remove its D.C. offset. The signals are then passed to an analogue-to-digital (A/D) converter 19 where they are converted to a digital format. The digital signals are then processed by the main processing unit (MPU) 20.

The main processing unit 20 controls the logic and circuitry of the bradycardia support pacing module 21, the antitachycardia pacing module 22 and the defibrillation module 23. The device 7 can be programmed by a telemetry link 25, and random access may be had to data storage registers or memory 26.

After being converted to digital form in A/D converter 19, data signals from the pressure sensing lead 15 are processed by a pressure processing unit (PPU) 24 that may be either a discrete circuit or a logical unit within the main processing unit 20. The pressure processing unit 24 is provided with a pressure processing unit memory 24a.

Figure 4:
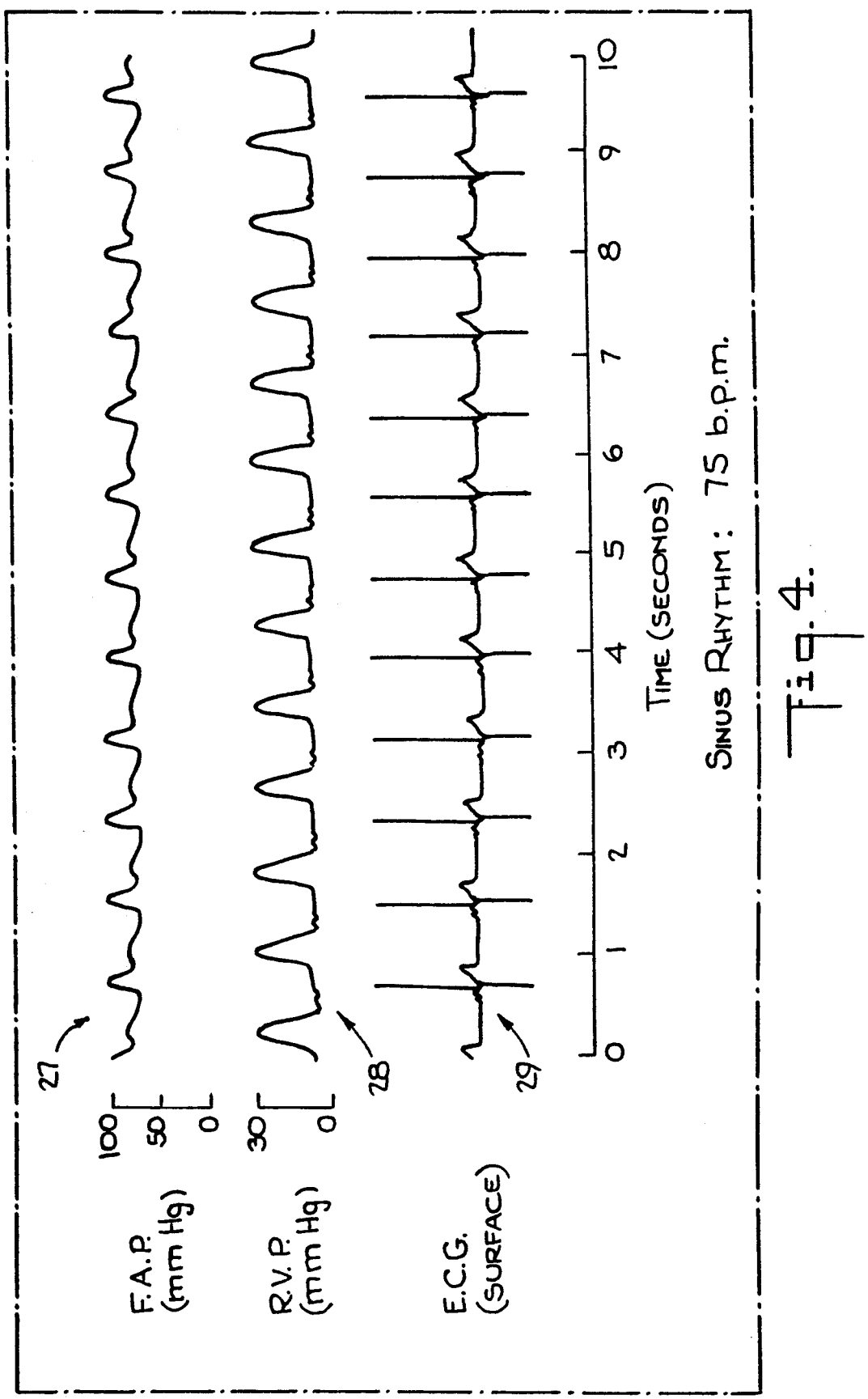
FIG. 4 is a representative diagram of normal femoral artery pressure, right ventricular pressure and ECG waveforms.

Referring now to FIG. 4, a typical RVP wave form is shown generally at 28, with the horizontal axis representing time in seconds, and the vertical axis representing the right ventricular pressure in millimeters of mercury. Similarly, a typical form of the pressure wave obtained in the femoral artery (FAP) is shown generally at 27, again with time being shown in seconds on the horizontal axis and the femoral artery pressure being shown in millimeters of mercury on the vertical axis. A surface ECG waveform is shown generally at 29, with time being shown on the horizontal scale and voltage being represented on the vertical scale. As may be seen by inspection of the various waveforms 27-29, the modulations of both pressure waveforms 27 and 28 fall between the R-waves of the ECG 29 during normal sinus rhythm at 75 bpm.

Figure 5:
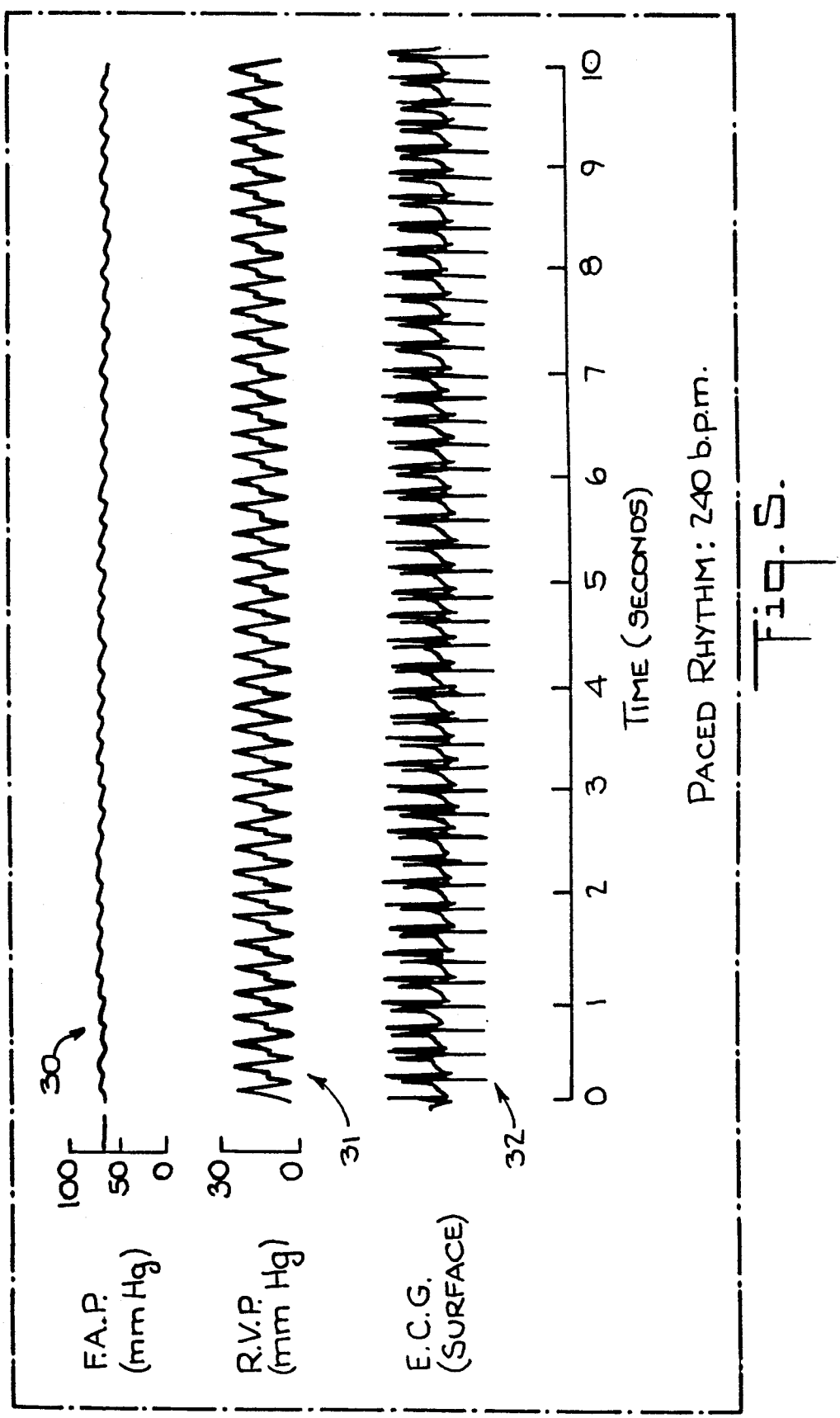
FIG. 5 is a representative diagram of femoral artery pressure, right ventricular pressure and ECG waveforms taken during ventricular pacing at 240 beats per minute (bpm)

Referring now to FIG. 5, the FAP waveform 30, the RVP waveform 31 and the ECG waveform 32 are shown with the corresponding heart beating at a paced rhythm of 240 bpm. As is apparent from an inspection of FIG. 5, the peak-to-peak amplitude of the RVP waveform 31 is well maintained even when the heart is paced to a high rate It can also be seen that, at this rate, the FAP waveform is low but still life sustaining in the short term. It can also be seen that the peaks of the right ventricle and femoral artery waveforms both occur after the R-wave of the ECG.

Figure 6:
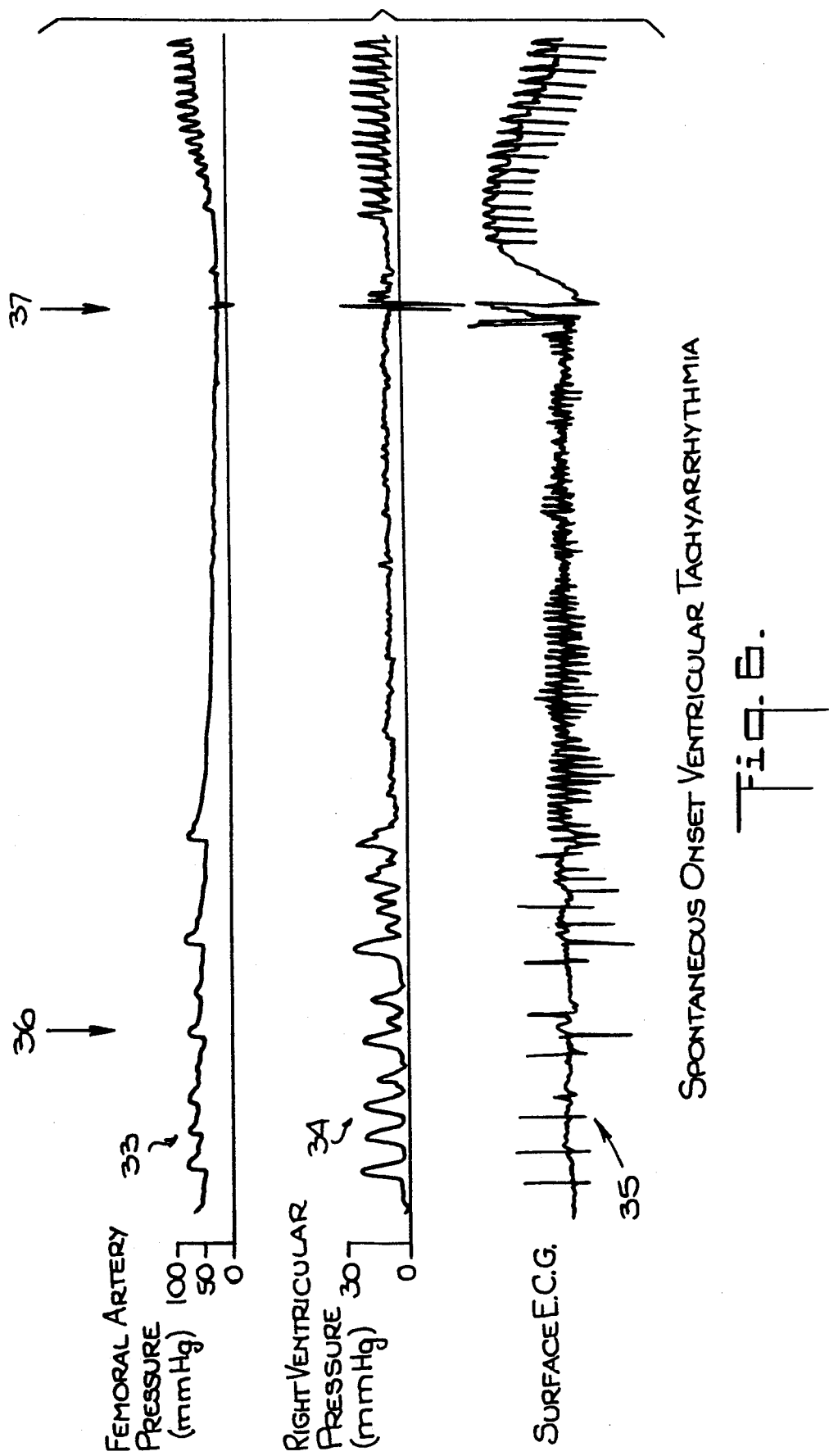
FIG. 6 is a representative diagram of femoral artery pressure, right ventricular pressure and ECG waveforms during an episode of ventricular fibrillation.

Referring now to FIG. 6, this figure depicts the typical changes in FAP waveform 33, RVP waveform 34 and ECG waveform 35 with the onset of ventricular fibrillation, shown at 36. It is noted that there is almost no modulation in either the RVP waveform 33 or the FAP waveform 34, and that the FAP is so low that life would cease unless action were taken. Normal function is returned after the administration of a defibrillating shock, shown at 37.

Referring back to FIG. 3, the pressure processing unit (PPU) 24 for the pressure waveform derives the right ventricular filtered peak-to-peak amplitude (RVFPPA) and the right ventricular peak pressure function (RVPPF) from the filtered and digitized right ventricular pressure (RVP) waveform. The PPU 24 communicates the derived data to the main processing unit (MPU) 20. The MPU 20 has access to the data registers (memory) 24a of the PPU 24.

The RVFPPA is obtained by filtering the RVP waveform with a high-pass filter having a 3 db frequency in the range of 0.1 to 0.5 Hz. In the preferred embodiments of the invention this filter is a second order Butterworth filter The RVFPPA is derived from the filtered RVP waveform by determining the maximum excursion of the filtered signal over a defined time period In the preferred embodiment this time period is determined by the period between R waves in the intracardiac ECG. The RVPPF is obtained by rectifying the filtered RVP waveform and then integrating it. The integral for each contraction is obtained by reference to the R-wave interval from the endocardial ECG. In the preferred embodiments of this device both the ECG signal and one or the other of the signals derived from the RVP waveform are used to determine whether or not the recipient of the device is haemodynamically compromised.

The device has two main implementations, each of which can be implemented using one of two algorithms. In the first algorithm (hereinafter referred to as the "simple threshold algorithm") the RVFPPA is monitored and compared to a threshold value to determine if haemodynamic compromise exists.

Figure 10:
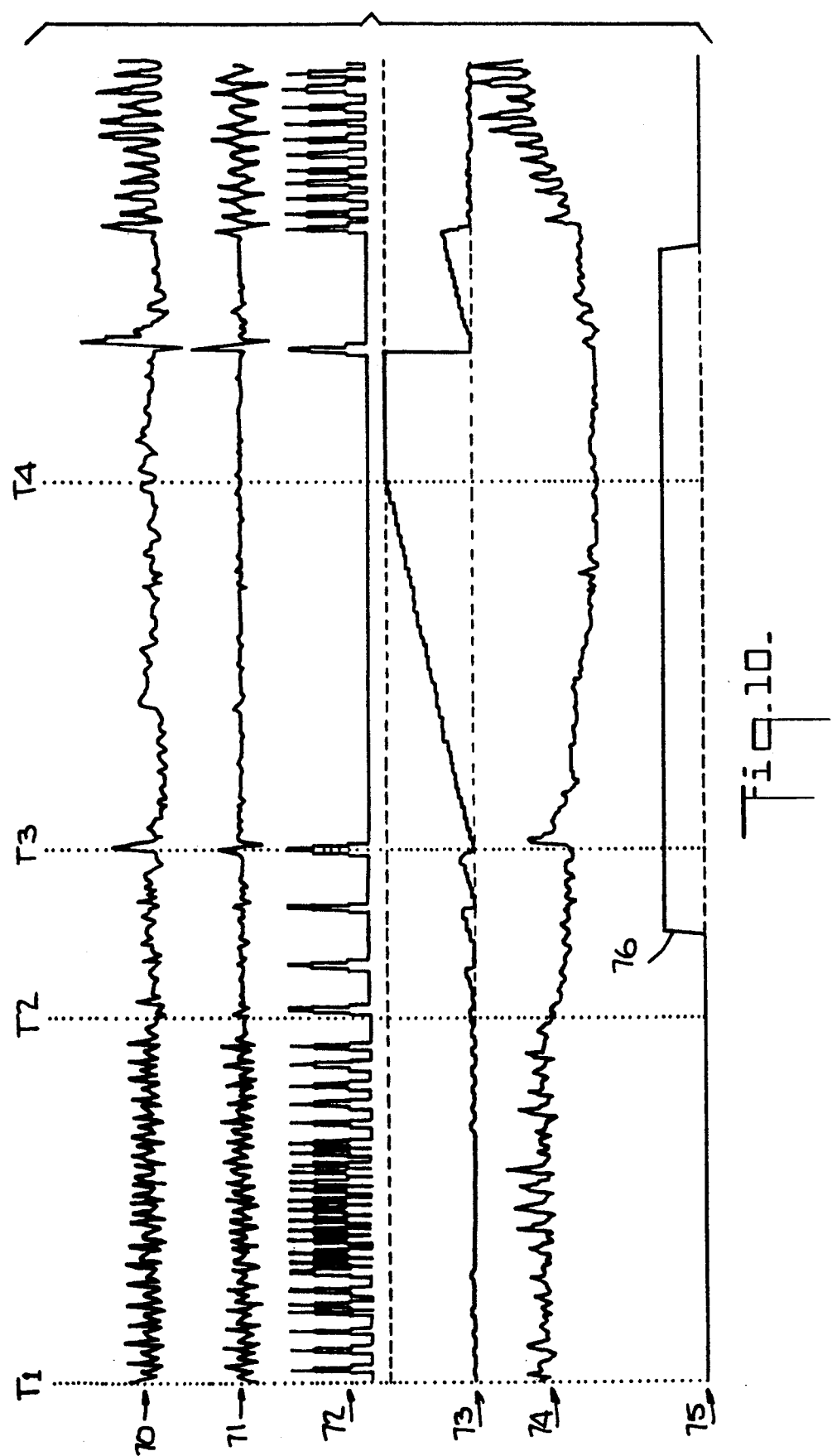

Referring to FIG. 10, representative traces of a number of concurrent signals taken during an electrophysiological study of a patient fitted with a device operating in accordance with the first algorithm have there been illustrated. An RVP trace is shown generally at 70. A trace of a filtered value of RVP is designated generally at 71. A trace of a comparison of the filtered waveform with a threshold value in a threshold detector is illustrated generally at 72. A trace from a simple counter is indicated generally at 73. A trace of the ventricular intracardiac ECG is shown generally at 74; and a trace, identified generally at 75, indicates when a high heart rate is detected by the MPU 20 and the PPU 24 of FIG. 3.

As shown in FIG. 10, the patient was first induced with pacing trains, starting at time T1, into a coarse ventricular tachycardia, which commences at time T2. The coarse ventricular tachycardia then degenerated into ventricular fibrillation, starting at time T3. This was reverted with defibrillation therapy, commencing at time T4. In operation, using the first, simple threshold, algorithm, the implantable cardioverting/defibrillating pacemaker device 7 (FIG. 3) of the present invention first transduces the RVP, as shown at 70, and filters it, as shown at 71. It then compares the filtered waveform with a threshold value, as shown at 72.

The threshold value is either a programmed value determined by the implanting physician or a derived parameter. The threshold detector 72 is linked to a simple counter 73 executed in software. Each time the value of the RVFPPA becomes greater than the threshold value, the counter is reset to zero. This counter increments each time the RVP is sampled. If this counter reaches a preprogrammed value, then haemodynamic compromise is deemed to exist. In such case the PPU 24 (FIG. 3) communicates this to the MPU 20. In the normally functioning recipient of this device, the rising edge of the RVFPPA would periodically reset the counter before the triggering value were reached.

Concurrently with the foregoing, the right ventricular intracardiac ECG is monitored, as shown at 74. When the MPU 20 (FIG. 3) detects a high rate in the intracardiac ECG, as shown at 76 in trace 75 of FIG. 10, and the PPU 24 is at the same time signifying that haemodynamic compromise exists, as indicated at time T4 when the counter trace 73 reaches its preprogrammed value, then the MPU initiates the appropriate therapy.

In the second algorithm (hereinafter referred as the "X out of Y algorithm"), the RVFPPA is assessed as a percentage of a programmed reference value and the values for the last "Y" beats are stored in memory, where "Y" is a programmed value. The RVPPF value is also calculated as a percentage of a programmed value and the values thereof for the last "Y" beats are also stored in memory.

If "X" out of the last "Y" beats, where "X" and "Y" are programmed values, fail to produce RVFPPA and/or RVPPF values above programmed levels, then the PPU 24 communicates this to the MPU 20, indicating that a state of haemodynamic compromise exists It is noted that for both detection algorithms the presence of a bradycardia is defined in terms of an electrically sensed bradycardia, with or without the pressure sensor detecting haemodynamic compromise. Asystole is defined in terms of the absence of electrical activity and of modulation in the RVFPPA.

The invention can be implemented in either of two embodiments, using either of the above algorithms. In the first embodiment of the device VFPPA and VPPF are continuously derived. In the second embodiment, the haemodynamic sensor is activated only when an electrical abnormality in the function of the heart is detected In the first embodiment the MPU 20 continuously monitors PPU 24, as well as the electrical activity of the heart. The result generated by the haemodynamic compromise detection algorithm is used in conjunction with information gained electrically about the heart rate to determine what therapy to initiate. Since both electrical and haemodynamic function of the heart are being continuously sensed, an abnormality in the function of either can initiate therapy In the first embodiment a pacing optimization algorithm is continuously active during bradycardia support pacing The use of pacing optimization in connection with bradycardia support pacing is described in the U.S. Pat. No. 4,869,252 of Norma L. Gilli, dated Sep. 26, 1989, which is entitled "Apparatus and Method for Controlling Pulse Energy in Antitachyarrhythmia and Bradycardia Devices" and is assigned to the assignee of the present invention. The disclosure of this patent is incorporated herein by reference. The use of different sensitivities to detect different conditions in electrically derived signals is described in the copending U.S. patent application Ser. No. 187,797 of R. Grevis and N. Gilli, filed Apr. 29, 1988, and entitled "Apparatus and Method for Controlling Multiple Sensitivities in Arrhythmia Control System Including Post-Therapy Pacing Delay," now U.S. Pat. No. 4,940,054, which description is also incorporated herein by reference.

When a tachyarrhythmia is detected in accordance with the first embodiment of the present invention, therapy is initiated in accordance with the chart set forth in FIG. 1. It is noted that the chart of FIG. 1 is based on the use of a heart rate of 120 bpm as the dividing point between a tachyarrhythmia condition requiring electrical shock therapy and a condition not requiring antitachyarrhythmia electrical shock therapy. This value is a programmable initialization variable that would be set by the user/clinician based on his knowledge of and experience with the patient. It should also be pointed out that the use of a dual chambered configuration allows a lower energy cardioversion shock to be used to revert an atrial fibrillation that is haemodynamically compromising. This arrhythmia is recognized by the presence of an atrial rate that is higher than the ventricular rate, in the presence of haemodynamic compromise.

In the second embodiment of this device the MPU 20 will activate the PPU 24 to derive one of the RVFPPA and RVPPF values and initiate the programmed pressure sensing algorithm, as above, in the event that the device senses an electrical disturbance of the heart. It will then initiate therapy in accordance with the chart of FIG. 1 No therapy will be initiated if there is no evidence of haemodynamic compromise. The MPU 20 also periodically activates the PPU 24 to ensure that the FPPA and VPPF are within optimal normal limits. If they are not, then the MPU 20 will initiate its pacing optimization algorithm.

Figure 7:
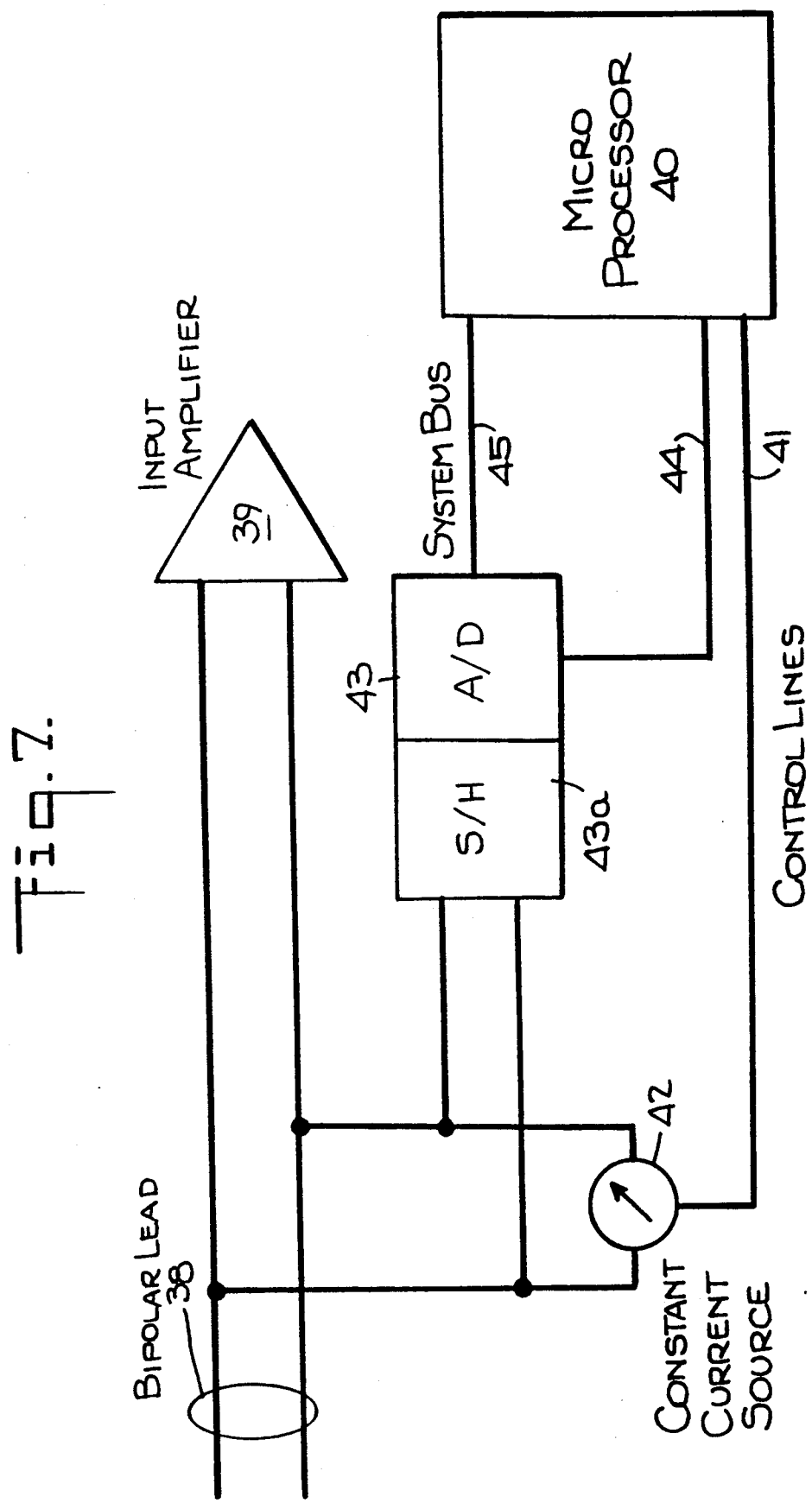
FIG. 7 is a schematic circuit diagram of a lead failure detection circuit that may be utilized in a device in accordance with the present invention.

The invention employs a system for detecting sensing modality failures. Referring to FIG. 7, the impedance of a bipolar sensing lead or sensor 38 is monitored, before connection to a sensing amplifier 39, by intermittently pulsing a known current down the sensor/lead and assessing the resulting voltage. In accordance with Ohms law, the impedance equals the sensed voltage divided by the pulse current (i.e., the sensed voltage is a measure of the lead impedance).

In the preferred embodiment the timing of the pulse of known current is controlled by microprocessor 40 via control lines 41 that control a constant current source 42. In an alternate embodiment, discrete timing circuitry may be used. Also, although a constant current source is used in the preferred embodiment, a constant voltage source could be used and the resulting current measured. An analog-to-digital (A/D) converter 43, having a built in sample and hold (S/H) circuitry 43a, is controlled via a control line 44. The signal on control line 44 is delayed so that the induced voltage is sampled just after the initiation of the pulse The held voltage is then converted to a digital value and this value is returned to the microprocessor via the system bus 45. The microprocessor 40 compares the sensed voltage with pre-programmed upper and lower reference values that are specific for the particular lead employed If the sensed value is outside these limits then the sensing modality is deactivated and the patient is delivered a tactile warning. The next time the device is accessed via telemetry, the attending physician is warned of the deactivation of the sensing modality Suitable circuitry for performing the sample and hold function is shown and described in the copending U.S. patent application Ser. No. 628,700, filed Dec. 14, 1990, of Alan H. Ostroff, entitled "Method and Device for Measuring Subthreshold Defibrillation Electrode Resistance and Providing a Constant Energy Shock Delivery", which is assigned to the Assignee of the present invention and is incorporated herein by reference.

A second method of verifying pressure transducer function comprises pacing the heart and determining whether or not there is a one to one correspondence between the number of pacing pulses delivered and the number of crossings of a programmed threshold pressure value observed In the event of deactivation of the pressure sensor logic, the invention relies solely on the electrically sensed heart rate to determine its function. In its operation based solely on the electrically sensed heart rate it performs in accordance with the disclosure of Grevis and Gilli in the aforesaid U.S. patent application No. 187,797.

In the event of there being a change in the impedance of the ECG sensing circuit to cause it to be outside of its operational limits, the device determines whether or not the delivery of pacing therapy is still possible This is done by pacing the heart and looking for an evoked pressure response that is determined by there being a rise in the highpass filtered RVP to above a threshold value in the period between each pacing pulse.

The pacing pulses are delivered to the heart at a rate of "K" bpm, such that they are delivered "A" milliseconds after the last sensed QRS complex. "K" in this case is a value programmed by the attending physician which would typically be 10-20 bpm greater than the resting heart rate. "A" in this case is a value programmed by the attending physician which would typically be 90% of the cycle length of the resting heart rate. To avoid precipitating a ventricular tachycardia, "A" must be sufficiently large so that the first pacing pulse is not delivered within the vulnerable R-T period of the preceding normal heartbeat. If pacing is not possible, then the patient is delivered a tactile warning The next time the device is accessed via telemetry, the attending physician is warned of this failure.

In the event of failure of the sensing of ECG and the ability to deliver pacing therapy, the device derives the heart rate by using an "X" out of "Y" detector based upon the time between crossings of the VF detection threshold. Should the pressure fall to below the VF detection threshold in the presence of an ECG lead failure, and provided that the impedance of the pressure sensor lead is within operating range, then the patient is assumed to be suffering a compromising ventricular tachyarrhythmia, and defibrillation therapy is commenced.

The attending physician has the ability to program the device to limit the number of defibrillation discharges delivered in such cases. After the delivery of the requisite number of defibrillation discharges, bradycardia support pacing is then initiated at the maximum possible pacing voltage.

Figure 8:
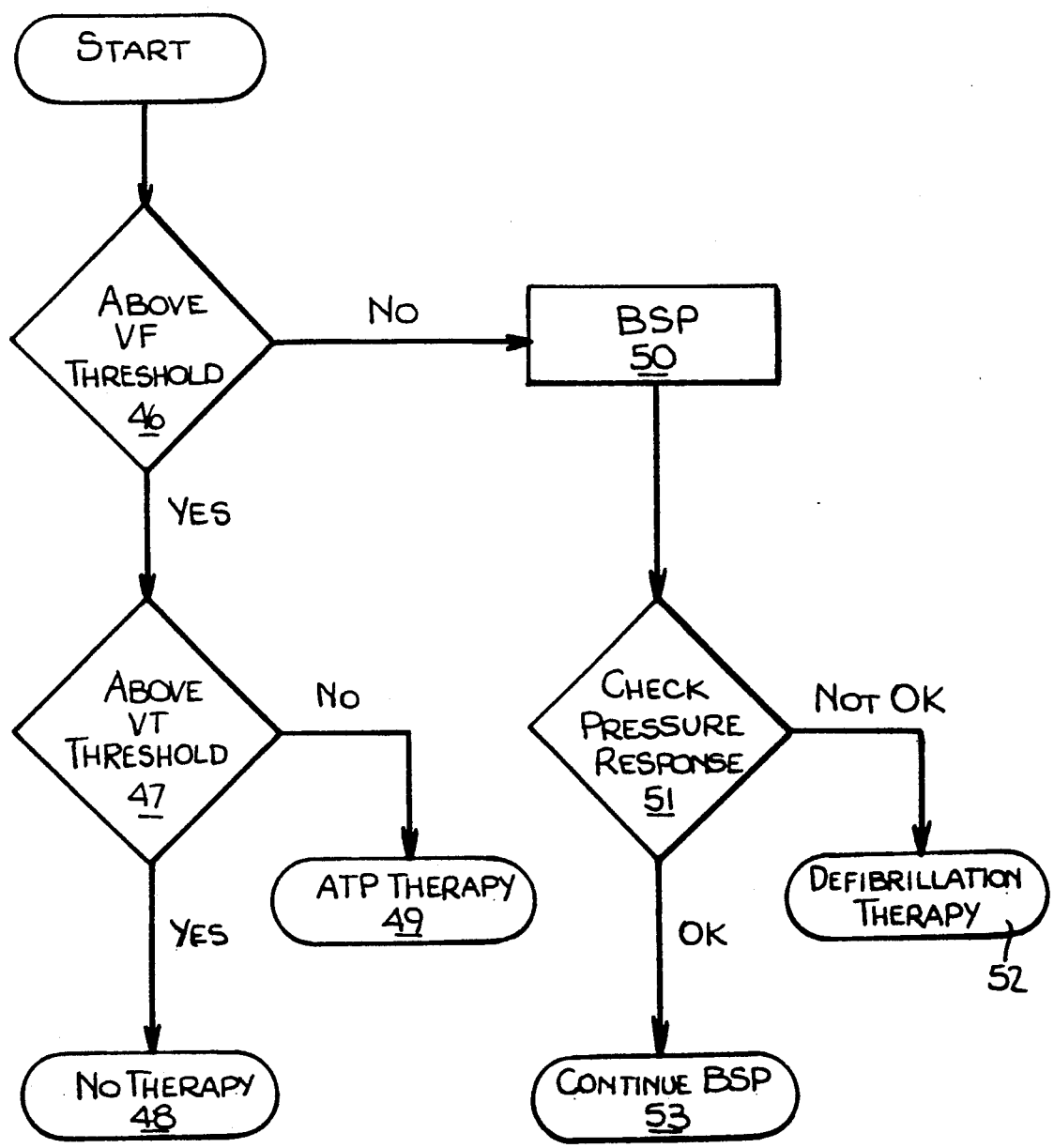
FIG. 8 is a logic flow diagram of a program that may be utilized for overcoming uncertainties in an electrical ECG diagnosis of the heart.

Referring now to FIG. 8, the methodology shown in this figure is employed to determine the state of the heart's function and the appropriate therapy to deliver, based upon the VP signal alone. This methodology is used when there is an uncertainty in the determination of the state of the heart's function based upon electrically derived heart rate criteria (e.g., noise injection detected), or a failure of the ECG sensing system. The methodology of FIG. 8 is activated only if the pressure sensing circuits are within operating impedance limits and the ECG circuit is at least capable of delivering pacing pulses.

As indicated earlier, in the preferred embodiment one of either the RVFPPA or the RVPPF are determined and assessed over a programmed time interval. As shown in the flowchart of FIG. 8, if during this interval the value of the selected one of the RVFPPA or the RVPPF is greater than both the VF detection threshold, as shown at 46, and the VT detection threshold, as shown at 47, then no pacing therapy is initiated, as shown at 48. If it is below the VT detection threshold but above the VF detection threshold, then antitachycardia pacing therapy is initiated, as shown at 49. If it is below the VF detection threshold, then bradycardia support pacing is initiated, as shown at 50, at the maximum possible voltage. If, in response to the initiation of bradycardia support pacing, there is no increase in the RVFPPA or RVPPF to above the VF detection limit, as shown at 51, then defibrillation therapy is initiated, as shown at 52. Bradyoardia support pacing is continued, as shown at 53, if an appropriate pressure response is detected within a programmed period after each pacing pulse is delivered.

Figure 9:
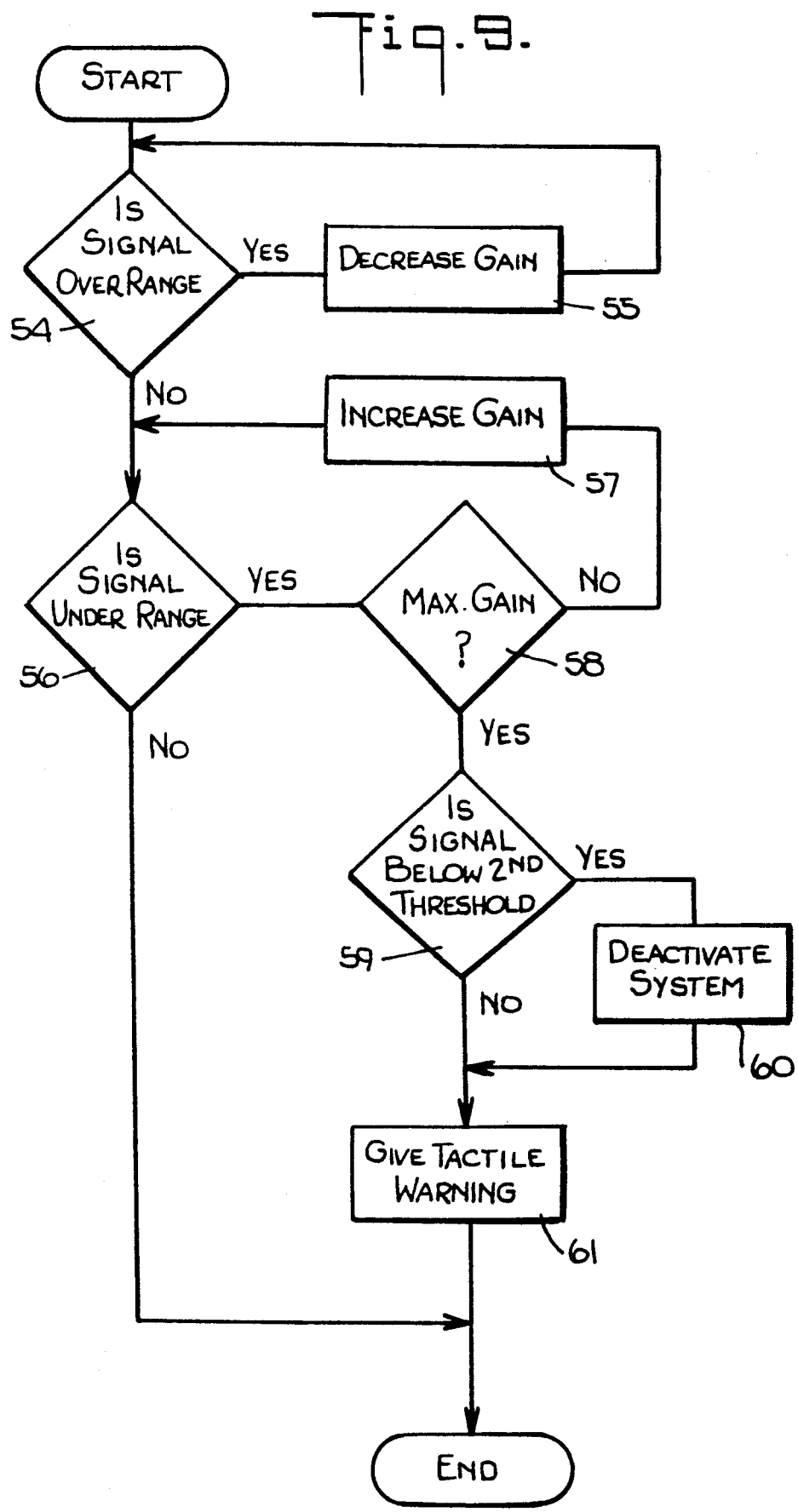
FIG. 9 is a logic flow diagram of a program that may be utilized for controlling the gain of ECG amplifiers based on information derived from the pressure waveform, and, FIG. 10 shows representative traces of a number of concurrent signals taken during an electrophysiological study of a patient fitted with a device in accordance with the present invention.

Referring to FIG. 9, the gains of the input sensing amplifiers 39 (FIG. 7) are routinely assessed at a programmed interval. This interval is accessible to programming by the implanting physician. Such assessments are made only in the event that both sensing systems are within normal impedance operating limits, and in the absence of abnormal heart function being detected in the sensing system that is not being manipulated. In the preferred embodiment the gain of ECG amplifier 39 is controlled by measuring the peak amplitude of the amplified ECG signal. If this amplitude is greater than the programmed upper operating limit of the amplifier, as shown at 54, than the gain of the amplifier is decreased, as shown at 55, until it is again within range If the peak amplitude of the amplified ECG signal is less than the programmed lower limit of amplifier 39, as shown at 56, and the gain of the amplifier is below its maximum gain as shown at 58, than the gain of the amplifier is increased, as shown at 57, until the amplified signal amplitude lies within the programmed range. If the maximum gain of the amplifier is reached, as shown at 58, and the amplified signal amplitude is still below the lower limit, than a comparison is made with a second programmed lower limit, as shown at 59, which limit is equal to or less than the first programmed lower limit. If the signal amplitude is below this second lower limit, then the ECG sensing system is deactivated, as shown at 60. The patient is then given a tactile warning, as shown at 61. In both cases, the next time the device is accessed via telemetry, the attending physician is warned of the falling ECG signal amplitude, and of the deactivation of the ECG sensing modality if this occurred.

In the preferred embodiment, the gain of the pressure sensing amplifiers is similarly controlled. In this case one of the resting RVFPPA or RVPPF maxima over a number of beats (5 in the preferred embodiment), is also stored as a reference value These values are accessible, via telemetry, to the attending physician at each review of device function, and provide a measure of the development of a fibrous sheath around the pressure sensor.

In another embodiment of the device, wherein ECG and pressure are both continuously monitored, the gain of the ECG input amplifiers is manipulated in a manner similar to that outlined above, even in the presence of a drop in the controlling or selected one of the RVFPPA or RVPPF to below the VT detection threshold In this case the amplitude of the ECG signal is accessed at a programmable frequency that would most typically be 1 Hz and the ECG sensing system is not deactivated in the event that the maximum gain setting is reached. In the event that the ECG-derived diagnosis is uncertain, or is at odds with the pressure derived diagnosis, the FIG. 8 method of deciding upon therapy is used. This method is not employed until the ECG amplitude has risen to within programmed limits, or the maximum gain setting of the ECG sensing amplifiers has been reached.

It will be apparent from the foregoing description that this invention provides for a variety of improved features in cardioverting/defibrillating pacemaker devices and methods Thus, the invention provides such a device and method which utilizes a second sensing modality and which is capable of determining the appropriate action to take in the event of a failure of or an uncertainty in the diagnosis of cardiac state in one of its two or more sensing systems. In addition, the invention provides a two sensing modality cardioverting/defibrillating pacemaker device which utilizes electrically derived timing events to diagnose heart function in the event of pressure signal failure and which, in the event of failure of the ECG sensing system, uses a VP signal to determine the state of function of the heart. Also, the invention provides such a device and method which can determine whether a malfunction which has developed is in the electrical signal sensing circuit and/or in the pacing circuitry, by reference to the evoked response seen in the ventricular pressure waveform. The invention then uses this information to alter its own therapy logic in order to best be able to deal with the detected malfunction. The invention further provides a cardioverting/defibrillating pacemaker device and method to implement a form of gain control that does not rely upon the signal being sensed to determine the state of heart function, while it ensures that the gain of the sensing amplifiers is optimal. Since two sensing modalities are employed, one signal is used to monitor the function of the heart while the gain of the other signal is being altered. Amplifier gain is thus controllable, and one of the two sensing systems can be deactivated when an adequate signal cannot be obtained in that system despite maximal amplifier gain. The invention further provides for a tactile warning to be given to the patient in the event that one of the two sensing modalities is deactivated, and the telemetry system will inform the supporting physician of this when he next interrogates the device.

While particular embodiments of this invention have been shown and described, it will be obvious to those skilled in the art that various other changes and modifications may be made without departing from this invention in its broader aspects, and it is, therefore, aimed in the appended claims to cover all such changes and modifications as fall within the true spirit and scope of this invention.

What is claimed is:

1. An implantable device for the treatment of tachyarrhythmia malfunctions of a patient's heart, said device including a first sensing means for sensing an electrical function in the patient's heart and providing a first signal representative of said electrical function, a second sensing means for sensing an haemodynamic function in the patient's heart and providing a second signal representative of said haemodynamic function, said second signal comprising either a ventricular filtered-peak-to-peak pressure amplitude, "VFPPA", or a ventricular peak pressure function, "VPPF", analyzing means primarily responsive to the signal from one of said sensing means for analyzing the state of the heart's function and providing any required electrical shock therapy to the heart, detecting means for detecting uncertainty in regard to the therapy to be provided to the heart by said analyzing means, and controlling means responsive to said uncertainty and operative to change the primary responsiveness of said analyzing means to the signal provided by the other of said sensing means for controlling the therapy that is to be provided to the heart.

2. An implantable device for the treatment of tachyarrhythmia malfunctions of a patient's heart, said device including a first sensing means for sensing an electrical function in the patient's heart and providing a first signal representative of said electrical function, a second sensing means for sensing an haemodynamic function in the patient's heart and providing a second signal representative of said haemodynamic function, said second signal comprising either a ventricular filtered-peak-to-peak pressure amplitude, "VFPPA", or a ventricular peak pressure function, "VPPF", analyzing means primarily responsive to the signal from one of said sensing means for analyzing the state of the heart's function and providing any required electrical shock therapy to the heart, detecting means for detecting uncertainty in regard to the therapy to be provided to the heart by said analyzing means, and controlling means responsive to said uncertainty and operative to change the primary responsiveness of said analyzing means to the signal provided by the other of said sensing means for controlling the therapy that is to be provided to the heart, said one of said sensing means being said first sensing means and said other of said sensing means being said second sensing means.

3. An implantable device for the treatment of tachyarrhythmia malfunctions of a patient's heart, said device including a first sensing means for sensing an electrical function in the patient's heart and providing a first signal representative of said electrical function, a second sensing means for sensing an haemodynamic function in the patient's heart and providing a second signal representative of said haemodynamic function, said second signal comprising either a ventricular filtered peak-to-peak pressure amplitude, "VFPPA", or ventricular peak pressure function, "VPPF", analyzing means primarily responsive to one of said signals for analyzing the state of the heart's function and providing any required electrical shock therapy to the heart, detecting means for detecting a malfunction of the sensing means which provides said one of said signals, and controlling means responsive to said malfunction and operative to change the primary responsiveness of said analyzing means to the sensing means which provides the other of said signals for controlling the therapy that is to be provided to the heart.

4. An implantable device for the treatment of tachyarrhythmia malfunctions of a patient's heart, said device including a first sensing means for sensing an electrical function in the patient's heart and providing a first signal representative of said electrical function, a second sensing means for sensing an haemodynamic function in the patient's heart and providing a second signal representative of said haemodynamic function, said second signal comprising either a ventricular filtered peak-to-peak pressure amplitude, "VFPPA", or ventricular peak pressure function, "VPPF", analyzing means primarily responsive to one of said signals for analyzing the state of the heart's function and providing any required electrical shock therapy to the heart, detecting means for detecting a malfunction of the sensing means which provides said one of said signals, and controlling means responsive to said malfunction and operative to change the primary responsiveness of said analyzing means to the sensing means which provides the other of said signals for controlling the therapy that is to be provided to the heart, said one of said sensing means being said first sensing means and said other of said sensing means being said second means.

5. A device according to any one of claims 1-4, wherein said first signal comprises an electrically derived ECG heart rate, wherein said device is implanted at a location remote from the heart, wherein each of said sensing means includes an electrical circuit, wherein each of said electrical circuits includes a sensor adapted to be inserted into a chamber of the heart, an amplifier positioned within said device remote from the heart and leads interconnecting said sensor with said amplifier, and wherein said controlling means includes means adapted to be coupled to said leads and operative to measure the impedance between said leads for deactivating a corresponding one of said sensing means in the event that said impedance is not within a predetermined range.

6. A device according to claim 5, wherein said controlling means further includes means responsive to changes in the measured impedance within the said predetermined range and operative to control the gain of said amplifiers for varying within predetermined limits the gain of said amplifiers relative to said changes in said impedance.

7. A device according to any one of claims 1-4, wherein said first signal comprises an electrically derived ECG heart rate, and wherein said first and second signals are sensed in the right ventricle of the patient's heart.

8. A device according to claim 7, further including a third sensing means for sensing an electrically derived ECG heart rate signal from the right atrium of the patient's heart.

9. A device according to any one of claims 1–4, wherein said first signal comprises an electrically derived ECG heart rate, and wherein said first and second signals are sensed in the left ventricle.

10. A device according to claim 9, and further including a third sensing means for sensing an electrically derived ECG heart rate signal from the left atrium of the patient's heart.

11. A device according to any one of claims 1–4, wherein said device includes means for providing bradycardia support pacing therapy to the heart, said device comprising a cardioverting/defibrillating pacemaker.

12. An implantable device for the treatment of malfunctions of a patient's heart, said device including a first sensing means for sensing an electrical function in the patient's heart and providing a first signal representative of said electrical function, a second sensing means for sensing an haemodynamic function in the patient's heart and providing a second signal representative of said haemodynamic function, said second signal comprising either a right ventricular filtered-peak-to-peak pressure amplitude, "RVFPPA", or a right ventricular peak pressure function, "RVPPF", analyzing means primarily responsive to the signal from one of said sensing means for analyzing the state of the heart's function and providing any required electrical shock therapy to the heart, detecting means for detecting uncertainty in regard to the therapy to be provided to the heart by said analyzing means, and controlling means responsive to said uncertainty and operative to change the primary responsiveness of said analyzing means to the signal provided by the other of said sensing means for controlling the therapy that is to be provided to the heart, said one of said sensing means being said first sensing means and said other of said sensing means being said second sensing means, said device further including means for comparing the level of either RVFPPA or RVPPF with a first predetermined threshold index thereof and detecting crossings of said threshold, and wherein said first signal comprises an electrically derived ECG heart rate and said second signal is representative of a right ventricular pressure waveform of the heart, wherein the state of the heart's function is determined from information derived from said second signal when there is uncertainty in the electrical diagnosis of said state, and wherein said analyzing means analyzes the state of the heart's function during periods of such uncertainty based on a comparison of the level of either RVFPPA or RVPPF with said first predetermined threshold index thereof, and (i) provides no therapy if said first threshold index is crossed repeatedly by said level within a programmed interval, (ii) provides ATP therapy if said level does not cross said first threshold index repeatedly during said programmed interval but crosses a second predetermined threshold index repeatedly during said programmed interval, (iii) provides bradycardia support pacing therapy if said level does not cross said second predetermined threshold index repeatedly during said programmed interval, and (iv) provides defibrillation therapy if an evoked pressure response is not sensed in response to said bradycardia support pacing.

13. A device according to claim 12, further including a third sensing means for sensing an electrically derived ECG heart rate signal from the right atrium of the patient's heart.

14. A device according to claim 13, wherein said device includes means for providing bradycardia support pacing therapy to the heart, said device comprising a cardioverting/defibrillating pacemaker.

15. A device according to claim 13, wherein said first signal comprises an electrically derived ECG heart rate, and wherein said device includes means for providing bradycardia support pacing therapy to the heart, said device comprising a cardioverting/defibrillating pacemaker.

16. A device according to claim 12, wherein said device includes means for providing bradycardia support pacing therapy to the heart, said device comprising a cardioverting/defibrillating pacemaker.

17. A method of treating tachyarrhythmia malfunctions of a patient's heart, comprising the steps of: implanting in a patient a device having a first means for sensing an electrical function in the patient's heart and providing a first signal representative of said electrical function, and having a second means for sensing an haemodynamic function in the patient's heart and providing a second signal representative of said haemodynamic function, said second signal comprising either a ventricular filtered peak-to-peak pressure amplitude, "VFPPA", or a ventricular peak pressure function, "VPPF"; analyzing one of said signals to determine the state of the heart's function, determine whether there is uncertainty in regard to a therapy to be provided to the heart and decide on any required electrical shock therapy to be provided to the heart; and, in the event of uncertainty in regard to the therapy to be provided as a result of said analysis, analyzing the other of said signals to decide on the electrical shock therapy to be provided to the heart.

18. A method of treating tachyarrhythmia malfunctions of a patient's heart, comprising the steps of: implanting in a patient a device having a first means for sensing an electrical function in the patient's heart and providing a first signal representative of said electrical function, and having a second means for sensing an haemodynamic function in the patient's heart and providing a second signal representative of said haemodynamic function, said second signal comprising either a ventricular filtered peak-to-peak pressure amplitude, "VFPPA", or a ventricular peak pressure function, "VPPF"; analyzing one of said signals to determine the state of the heart's function, determine whether there is uncertainty in regard to a therapy to be provided to the heart and decide on any required electrical shock therapy to be provided to the heart; and, in the event of uncertainty in regard to the therapy to be provided as a result of said analysis, analyzing the other of said signals to decide on the electrical shock therapy to be provided to the heart, said one of said signals being said first signal and other said of said signals being said second signal.

19. A method of treating malfunctions of a patient's heart, comprising the steps of: implanting in a patient a device having a first means for sensing an electrical function in the patient's heart and providing a first signal representative of said electrical function, a second means for sensing an haemodynamic function in the patient's heart and providing a second signal representative of said haemodynamic function, said second signal comprising either a ventricular filtered-peak-to-peak pressure amplitude, "VFPPA", or a ventricular peak pressure function, "VPPF"; analyzing one of said signals to determine the state of the heart's function, determine whether a malfunction exists in the sensing means which provides said one of said signals and decide on any required electrical shock therapy to be provided to the heart; and, in the event of a malfunction in the sensing means which provides said one of said signals, analyzing the other said signals to decide on the electrical shock therapy to be provided to the heart.

20. A method of treating malfunctions of a patient's heart, comprising the steps of: implanting in a patient a device having a first means for sensing an electrical function in the patient's heart and providing a first signal representative of said electrical function, a second means for sensing an haemodynamic function in the patient's heart and providing a second signal representative of said haemodynamic function, said second signal comprising either of a ventricular filtered-peak-to-peak pressure amplitude, "VFPPA", or a ventricular peak pressure function, "VPPF"; analyzing one of said signals to determine the state of the heart's function, determine whether a malfunction exists in the sensing means which provides said one of said signals and decide on any required electrical shock therapy to be provided to the heart; and, in the event of a malfunction in the sensing means which provides said one of said signals, analyzing the other said signals to decide on the electrical shock therapy to be provided to the heart, said one of said signals being said first signal and said other of said signals being said second signal.

21. A method according to any one of claims 17–20, wherein said first signal comprises an electrically derived ECG heart rate, wherein said device includes means for providing bradycardia support pacing therapy to the heart, wherein said device is a cardioverting-/defibrillating pacemaker implanted in the patient at a location remote from the patient's cardiac cavity, wherein said device is provided with sensing leads which interconnect the chambers of the patient's heart with electrical sensing circuits in the first and second sensing means of said device, and wherein said method further includes the steps of checking that the impedances of said sensing leads are within predetermined limits; and deactivating one or the other of said sensing means if the impedance of its sensing leads is not within said predetermined limits.

22. A method according to any one of claims 17–20, wherein said first signal comprises an electrically derived ECG heart rate, wherein said electrical sensing circuits include sensing amplifiers, and wherein said method further includes the step of varying the gains of said sensing amplifiers within predetermined limits to compensate for changes in the impedances of said sensing leads.

23. A method of treating malfunctions of a patient's heart, comprising the steps of: implanting in a patient a device having a first means for sensing an electrical function in the patient's heart and providing a first signal representative of said electrical function, and having a second means for sensing an haemodynamic function in the patient's heart and providing a second signal representative of said haemodynamic function, said second signal comprising either a ventricular filtered peak-to-peak pressure amplitude, "VFPPA", or a ventricular peak pressure function, "VPPF"; analyzing one of said signals to determine the state of the heart's function, determine whether there is uncertainty in regard to a therapy to be provided to the heart and decide on any required electrical shock therapy to be provided to the heart; and, in the event of uncertainty in regard to the therapy to be provided as a result of said analysis, analyzing the other of said signals to decide n the electrical shock therapy to be provided to the heart, wherein said first signal comprises an electrically derived ECG heart rate, wherein said device is a cardioverting/defibrillating pacemaker implanted in the patient at a location remote from the patient's cardiac cavity, wherein said device is provided with sensing leads which interconnect the chambers of the patient's heart with respect to first and second electrical sensing circuits in the first and second sensing means of said device, wherein said electrical sensing circuits include corresponding sensing amplifiers, and wherein said method further includes the steps of: periodically assessing the impedance of the ECG sensing leads to insure that it is within predetermined limits; periodically assessing the amplitude of the amplified ECG signal outputted by the ECG sensing amplifier and adjusting the gain of said sensing amplifier to ensure that said output of said amplifier is maintained within predetermined limits; and, establishing that the patient's heart is in a state of normal function both before and during the adjustment of the gain of the ECG sensing amplifier by relying on haemodynamic heart function information obtained from said second signal.

24. A method of treating malfunctions of patient's heart, comprising the steps of: implanting in a patient a device having a first means for sensing an electrical function in the patient's heart and providing a first signal representative of said electrical function, and having a second means for sensing an haemodynamic function in the patient's heart and providing a second signal representative of said haemodynamic function, said second signal comprising either a ventricular filtered peak-to-peak pressure amplitude, "VFPPA", or a ventricular peak pressure function, "VPPF"; analyzing one of said signals to determine the state of the heart's function, determine whether there is uncertainty in regard to a therapy to be provided to the heart and decide on any required electrical shock therapy to be provided to the heart; and, in the event of uncertainty in regard to the therapy to be provided as a result of said analysis, analyzing the other of said signals to decide on the electrical shock therapy to be provided to the heart, wherein said device is a cardioverting/defibrillating pacemaker implanted in the patient at a location remote from the patient's cardiac heart cavity, wherein said device is provided with ventricular pressure, "VP", sensing leads which interconnect chambers of the patient's heart with respect to first and second electrical sensing circuits in the first and second sensing means of said device, wherein said electrical sensing circuits include corresponding sensing amplifiers, and wherein said method further includes the steps of: periodically assessing the impedance of the VP sensing leads to ensure that it is within predetermined limits; periodically assessing the amplitude of the amplified VP signal outputted by the VP sensing amplifier and adjusting the gain of said sensing amplifier to ensure that said output of said amplifier is maintained within predetermined limits; and establishing that the patient's heart is in a state of normal function both before and during the adjustment of the gain of the VP sensing amplifier by relying upon ECG heart function information obtained from said first signal.

25. A method of treating malfunctions of a patient's heart, comprising the steps of: implanting in a patient a device having a first means for sensing an electrical function in the patient's heart and providing a first signal representative of said electrical function, and having a second means for sensing an haemodynamic function in the patient's heart and providing a second signal representative of said haemodynamic function, said second signal comprising either a ventricular filtered peak-to-peak pressure amplitude, "VFPPA", or a ventricular peak pressure function, "VPPF"; analyzing one of said signals to determine the state of the heart's function, determine where there is uncertainty in regard to a therapy to be provided to the heart and decide on any required electrical shock therapy to be provided to the heart; and, in the event of uncertainty in regard to the therapy to be provided as a result of said analysis, analyzing the other of said signals to decide on the electrical shock therapy to be provided to the heart, wherein said device is a cardioverting/defibrillating pacemaker, wherein said second signal is representative of the right ventricular pressure waveform of the heart, wherein the state of the heart's function is derived from said second signal when there is an uncertainty in the diagnosis of said state as derived from said first signal, and wherein said method further includes the steps of: analyzing the state of the heart's function during periods of such uncertainty based on a comparison of the level of either right VFPPA or right VPPF with a first predetermined threshold index thereof, and (i) providing no therapy if said first threshold index is crossed repeatedly by said level within a programmed interval, (ii) providing ATP therapy if said level does not cross said first threshold index repeatedly during said programmed interval but crosses a second predetermined threshold index repeatedly during said programmed interval, (iii) providing bradycardia support pacing therapy if said level does not cross said second predetermined threshold index repeatedly during said programmed interval, and (iv) providing defibrillation therapy if an evoked pressure response is not sensed in response to said bradycardia support pacing.

26. A method of treating malfunctions of a patient's heart, comprising the steps of: implanting in a patient a device having a first means for sensing an electrical function in the patient's heart and providing a first signal representative of said electrical function, and having a second means for sensing a haemodynamic function in the patient's heart and providing a second signal representative of said haemodynamic function, said second signal comprising one or another of a ventricular filtered peak-to-peak pressure amplitude, "VFPPA", or a ventricular peak pressure function, "VPPF"; analyzing one of said signals to determine the state of the heart's function, determine whether there is uncertainty in regard to a therapy to be provided to the heart and decide on any required electrical shock therapy to be provided to the heart; and, in the event of uncertainty in regard to the therapy to be provided as a result of said analysis, analyzing the other of said signals to decide on the electrical shock therapy to be provided to the heart, wherein said device is implanted in the patient at a location remote from the patient's cardiac cavity, wherein said device is provided with sensing leads which interconnect chambers of the patient's heart with electrical sensing circuits in the first and second sensing means of said device, and wherein said method further includes the steps of checking that the impedance of said ECG sensing leads is within predetermined limits and, if it is not, then determining whether or not pacing is still possible by applying a short train of pacing pulses at a preprogrammed rate and checking for ventricular pressure responses thereto; if pacing is determined to still be possible, altering control of the device so that it relies solely upon pressure derived information to determine the state of the heart's function; and, providing a warning signal to alert the patient or his attending physician of a system failure.

27. A method of treating malfunctions of a patient's heart, comprising the steps of: implanting in a patient a device having a first means for sensing an electrical function in the patient's heart and providing a first signal representative of said electrical function, a second means for sensing an haemodynamic function in the patient's heart and providing a second signal representative of said haemodynamic function, said second signal comprising either a ventricular filtered-peak-to-peak pressure amplitude, "VFPPA", or a ventricular peak pressure function, "VPPF"; analyzing one of said signals to determine the state of the heart's function, determine whether a malfunction exists in the sensing means which provides said one of said signals and decide on any required electrical shock therapy to be provide to the heart; and, in the event of a malfunction in the sensing means which provides said one of said signals, analyzing the other said signals to decide on the electrical shock therapy to be provided to the heart, wherein said first signal comprises an electrically derived ECG heart rate, wherein said device is a cardioverting/defibrillating pacemaker implanted in the patient at a location remote from the patient's cardiac cavity, wherein said device is provided with sensing leads which interconnect the chambers of the patient's heart with respect to first and second electrical sensing circuits in the first and second sensing means of said device, wherein said electrical sensing circuits include corresponding sensing amplifiers, and wherein said method further includes the steps of: periodically assessing the impedance of the ECG sensing leads to insure that it is within predetermined limits; periodically assessing the amplitude of the amplified ECG signal outputted by the ECG sensing amplifier and adjusting the gain of said sensing amplifier to ensure that said output of said amplifier is maintained within predetermined limits; and, establishing that the patient's heart is in a state of normal function both before and during the adjustment of the gain of the ECG sensing amplifier by relying on haemodynamic heart function information obtained from said second signal.

28. A method of treating malfunctions of a patient's heart, comprising the steps of: implanting in a patient a device having a first means for sensing an electrical function in the patient's heart and providing a first signal representative of said electrical function, a second means for sensing an haemodynamic function in the patient's heart and providing a second signal representative of said haemodynamic function, said second signal comprising either a ventricular filtered-peak-to-peak pressure amplitude, "VFPPA", or a ventricular peak pressure function, "VPPF"; analyzing one of said signals to determine the state of the heart's function, determine whether a malfunction exists in the sensing means which provides said one of said signals and decide on any required electrical shock therapy to be provided to the heart; and, in the event of a malfunction in the sensing means which provides said one of said signals, analyzing the other said signals to decide on the electrical shock therapy to be provided to the heart, wherein said device is a cardioverting/defibrillating pacemaker implanted in the patient at a location remote from the patient's cardiac heart cavity, wherein said device is provided with ventricular pressure, "VP", sensing leads which interconnect chambers of the patient's heart with respect to first and second electrical sensing circuits in the first and second sensing means of said device, wherein said electrical sensing circuits include corresponding sensing amplifiers, and wherein said method further includes the steps of: periodically assessing the impedance of the VP sensing leads to ensure that it is within predetermined limits; periodically assessing the amplitude of the amplified VP signal outputted by the VP sensing amplifier and adjusting the gain of said sensing amplifier to ensure that said output of said amplifier is maintained within predetermined limits; and establishing that the patient's heart is in a state of normal function both before and during the adjustment of the gain of the VP sensing amplifier by relying upon ECG heart function information obtained from said first signal.

29. A method of treating malfunctions of a patient's heart, comprising the steps of: implanting in a patient a device having a first means for sensing an electrical function in the patient's heart and providing a first signal representative of said electrical function, a second means for sensing an haemodynamic function in the patient's heart and providing a second signal representative of said haemodynamic function, said second signal comprising either a right ventricular filtered-peak-to-peak pressure amplitude, "RVFPPA", or a right ventricular peak pressure function, "RVPPF"; analyzing one of said signals to determine the state of the heart's function, determine whether a malfunction exists in the sensing means which provides said one of said signals and decide on any required electrical shock therapy to be provided to the heart; and, in the event of a malfunction in the sensing means which provides said one of said signals, analyzing the other said signals to decide on the electrical shock therapy to be provided to the heart, wherein said device is a cardioverting/defibrillating pacemaker, wherein said second signal is representative of the right ventricular pressure waveform of the heart, wherein the state of the heart's function is derived form said second signal when there is an uncertainty in the diagnosis of said state as derived from said first signal, and wherein said method further includes the steps of: analyzing the state of the heart's function during periods of such uncertainty based on a comparison of the level of either RVFPPA or RVPPF with a first predetermined threshold index thereof and (i) providing no therapy if said first threshold index is crossed repeatedly by said level within a programmed interval, (ii) providing ATP therapy if said level does not cross said first threshold index repeatedly during said programmed interval but crosses a second predetermined threshold index repeatedly during said programmed interval, (iii) providing bradycardia support pacing therapy if said level does not cross said second predetermined threshold index repeatedly during said programmed interval, and (iv) providing defibrillation therapy if an evoked pressure response is not sensed in response to said bradycardia support pacing.

30. A method of treating malfunctions of a patient's heart, comprising the steps of: implanting in a patient a device having a first means for sensing an electrical function in the patient's heart and providing a first signal representative of said electrical function, a second means for sensing an haemodynamic function in the patient's heart and providing a second signal representative of said haemodynamic function, said second signal comprising either a ventricular filtered-peak-to-peak pressure, "VFPPA", or a ventricular peak pressure function, "VPPF"; analyzing one of said signals to determine the state of the heart's function, determine whether a malfunction exists in the sensing means which provides said one of said signals and decide on any required electrical shock therapy to be provided to the heart; and, in the event of a malfunction in the sensing means which provides said one of said signals, analyzing the other said signals to decide on the electrical shock therapy to be provided to the heart, wherein said device is implanted in the patient at a location remote from the patient's cardiac cavity, wherein said device is provided with sensing leads which interconnect chambers of the patient's heart with electrical sensing circuits in the first and second sensing means of said device, and wherein said method further includes the steps of checking that the impedance of said ECG sensing leads is within predetermined limits and, if it is not, then determining whether or not pacing is still possible by applying a short train of pacing pulses at a pre-programmed rate and checking for ventricular pressure responses thereto; if pacing is determined to still be possible, altering control of the device so that it relies solely upon pressure derived information to determine the state of the heart's function; and, providing a warning signal to alert the patient or his attending physician of a system failure.

31. A method according to any one of claims 23-30, wherein said one of said signals is said first signal and said other of said signals is said second signal.

* * * * *